United States Patent [19]

Costanzi et al.

[11] 4,325,864

[45] Apr. 20, 1982

[54] PYRROLIDINE-RING-CONTAINING COMPOSITIONS FOR USE AS ANTI-UV STABILIZERS IN PLASTICS MATERIALS

[75] Inventors: Silvestro Costanzi, San Giuliano Milanese; Francesco Tessarolo, Monza; Adriano Ballabio, Giussano, all of Italy

[73] Assignee: ANIC S.p.A., Palermo, Italy

[21] Appl. No.: 213,653

[22] Filed: Dec. 5, 1980

[30] Foreign Application Priority Data

Feb. 19, 1980 [IT] Italy ................................. 20001 A/80

[51] Int. Cl.³ ........................ C08K 5/00; C07D 207/08
[52] U.S. Cl. ................................ 524/104; 260/326.43
[58] Field of Search ............ 260/326.43, 23 H, 45.8 N

[56] References Cited

FOREIGN PATENT DOCUMENTS 923915  7/1949  Fed. Rep. of Germany ................. 260/326.43

*Primary Examiner*—Jane T. Fan
*Attorney, Agent, or Firm*—Morgan, Finnegan, Pine, Foley & Lee

[57] ABSTRACT

For stabilizing polyolefin polymers such as polyethylene and polypropylene against the detrimental effects of exposure to UV-radiations and weathering agents, a stabilizing additive is disclosed which consist of a fatty acid ester of the N-(beta-hydroxyethyl)-2,2,3,4,5,5-hexamethylpyrrolidine. The lauric and palmitic acid esters are preferred.

5 Claims, No Drawings

PYRROLIDINE-RING-CONTAINING COMPOSITIONS FOR USE AS ANTI-UV STABILIZERS IN PLASTICS MATERIALS

This invention relates to novel pyrrolidine-ring-containing compositions for use as stabilizing agents against the action of UV-radiations on plastics materials, such as polyolefins and more particularly polyethylene and polypropylene.

It is well known that polyolefins, such as polypropylene and polyethylene exhibit a tendency towards decay under the action of radiations, especially UV-radiations and of weathering agents in general.

Such a degradation unfolds itself with the loss of certain physical properties of the polymers, such as a decrease of the tensile strength and a loss of pliability.

The decay of the properties indicated above can quantitatively be assessed by determining the viscosity index of the polymers in the molten state, that is, the Melt Flow Index, MFI.

An exceedingly high increase of the MFI denounces a considerable degradation of the polymer concerned.

In order that such a degradation may be prevented, it has been common practice to add to the polymers small amounts of stabilizing compounds, care being taken that the compounds in question were not such as to alter the other properties of the polymers so treated.

It has now been found, that which is the subject matter of this invention, that novel compositions which contain the pyrrolidine ring and which are sterically hindered at the N-atom, have excellent stabilizing properties against the action of UV-radiations in polyolefins, such as polyethylene and polypropylene.

The preparation of such novel compositions will be described hereinafter.

The compounds according to this invention are fatty acid esters of the N-(beta-hydroxyethyl)-2,2,3,4,5,5,-hexamethylpyrrolidine, wherein the esterifying fatty acids are, for example, butyric, palmitic, lauric, stearic acid and like acids.

Their preparation can be carried out with conventional procedures, such as, for example, the methods by Hennion and Di Giovanna, as reported in the Journal of Organic Chemistry, August 1965, pages 2645 and seqq.

In order that the subject matter of the invention and its objects may be better understood, a few examples will be set forth hereinafter, which are illustrative of the syntheses of the lauric acid and palmitic acid esters of the N-(beta-hydroxyethyl)-hexamethylpyrrolidine, and of their practical use as anti-UV stabilizers for propylene.

EXAMPLE 1

Preparation of the 2,2,3,4,5,5-hexamethylpyrrolidine 70 g (grams) of di-tert.propargylamine have been dissolved in 300 mls (millilitres) of acetic acid and charged in an autoclave together with 50 g of a Pd-based catalyst supported on activated charcoal, the Pd content being 5% by wt.

The reaction mixture has been maintained under hydrogen pressure at room temperature and subsequently the temperature has been raised to 140° C. until no absorption of hydrogen has been observed any more.

Eventually, the reaction mixture has been brought back to room temperature and filtered, to remove the catalyst therefrom.

The filtrate has been made alkaline with a 30% aqueous solution of NaOH and twice extracted with ethyl ether.

The ethereal extracts have been combined and dried over NaOH and evaporated to dryness.

The expected product has been obtained as a mixture of stereo-isomerides and has a boiling point (b.p.) temperature of 65° C.–70° C. under an absolute pressure of 15 mmHg (millimeters of mercury). (The literature data are 70° C.–74° C. under 20 mmHg). The product has been obtained with a yield of 50% relative to the starting product.

The product has been identified by mass-spectroscopy and NMR analysis.

EXAMPLE 2

Preparation of the N-(beta-hydroxyethyl)-2,2,3,4,5,5-hexamethylpyrrolidine.

The compound obtained in Example 1 hereof has been N-substituted (hydroxyethylated) with a conventional method by chargin an autoclave with 15 g of hexamethylpyrrolidine with 20 mls water and ethylene oxide in an amount which slightly exceeded the stoichiometric quantity.

After a four-hour reaction at 120° C., the organic layer has been separated and distillation has been carried out.

The expected N-(beta-hydroxyethyl)-2,2,3,4,5,5-hexamethylpyrrolidine has been obtained with a yield of over 90%, in the form of a colorless viscous liquid having a b.p of 80° C.–83° C. under an abs.pressure of 3 mmHg.

EXAMPLE 3

Preparation of the 2,2,3,4,5,5,-hexamethylpyrrolidine-N-ethyl-2-lauric acid ester.

50 g of N-(beta-hydroxyethyl)-2,2,3,4,5,5-(hexamethyl)-pyrrolidine (a mixture of the stereo-isomerides), prepared as described hereinabove have been introduced in a flask together with 300 mls of benzene and 35 mls of triethylamine.

40 g of lauroyl chloride have been introduced through a dropping funnel and the temperature has been raised to 80° C.–90° C.

The reaction mixture has been allowed to react at the temperature specified above until such time as all the N-(beta-hydroxyethyl)-2,2,3,4,5,5-(hexamethyl)-pyrrolidine was discharged, that which required 5 hours approximately.

The reaction mixture has subsequently been filtered to remove the solids, and eventually distilled.

The expected product has been obtained with a yield of over 90%. It was a transparent viscous liquid, having a light straw-yellow color and a b.p. of 187° C.–190° C. under a pressure of $5.10^{-2}$ mmHg.

The analytical check for identifying the product has been made by InfraRed spectrometry.

The corresponding palmitic acid ester has been prepared in a like manner, using 50 g of palmitoyl chloride as the starting material.

Such palmitic acid ester, the identity of which has been confirmed by InfraRed spectrometry, had a b.p. of 220° C.–225° C. under a pressure of $5.10^{-2}$ mmHg.

The thusly obtained esterified products have been exploited for the stabilization of polypropylene, and the protective activity has been assessed in comparison with customary stabilizers in current commercial use, such as benz-triazole(Tinuvin P,Trade Mark) and benzophenone(Tinuvin 531,Trade Mark), according to the testing procedure specified hereinafter.

General-Purpose polypropylene, already compounded with the conventional stabilizers and processing aids has been supplemented in five different portions with an anti-UV stabilizer: the anti-UV stabilizers tested were: hexamethylpyrrolidine ehtyl laurate (1), hexamethylpyrrolidine ehtyl palmitate (2) in amounts of 0.9% by wt and 1% by wt, benz-triazole(Tinuvin P,Trade Mark) in an amount of 0.5% by wt and benzophenone (Tinuvin 531,Trade Mark) also in the amount of 0.5% by wt.

The two commercial anti-UV stabilizers have been added in the amount of 0.5% by wt, because this is the value which is currently suggested by manufacturers.

The blending of the anti-UV stabilizing agents has been carried out according to the procedures which are conventionally used for incorporating stabilizers in polyolefins, that is, in a roll mill at 180° C. for 5 mins.

0.5-mm thick platelets have then been prepared in a compression press at 180° C. with the following cyclical sequence; 5-minute preheating-5-minute pressing. The thusly prepared platelets have been exposed in an Atlas (TradeMark)Weatherometer having two arc lamps with emission peaks at 3,600–3,850 and 4,200 Angstrom Units with rain cycle (102 minutes light, 18 minutes rain).

The resistance of polypropylene to exposure to UV-radiations has been assessed by viscosity measurements (Melt Flow Index, MFI) according to the testing prescriptions of Specification ASTM D-1238 after the several exposure times.

In the attached Table, the MFI trends of the several polypropylene samples with increasing exposure times are tabulated.

The improved constancy of the MFI values for the polymers supplemented with the stabilizers of the present invention, as compared with the commercial stabilzers, can readily be appreciated.

With the commercial stabilizers, tre viscosity index trend is irregular and shows an abrupt increase in correspondence with prolonged UV-exposure.

Tests performed with higher amounts of benztriazole (1% by wt) have even shown that this commercial product has even a destabilizing action if higher concentration levels are adopted.

These facts are nothing but a confirmation of the improved stabilizing effect afforded by the anti-UV stabilizers according to this invention whenever comparatively long exposure times to weathering agents are experienced.

| Melt Flow Index Trend General Purpose Polypropylene with various anti-UV stabilizers | | | | | | |
|---|---|---|---|---|---|---|
| | MFI | | | | | |
| Exposure time, hours | 0 Start | 500 | 750 | 1,000 | 1,250 | 1,800 |
| POLYPROPYLENE, as such | 3.8 | 4.8 | 5.7 | 7 | 9 | 50 |
| POLYPROPYLENE + 0.9% ethyl laurate(1) | 3.8 | — | 5.5 | 8 | 8.5 | 8.5 |
| POLYPROPYLENE + 1% eth. palmitate(2) | 3.7 | 4.5 | 5.8 | 7.5 | 8 | 8.4 |
| POLYPROPYLENE + 0.5% benz-triazole (Tinuvin P) | 3.6 | 5.1 | 5.2 | 6 | 6.5 | 23 |
| POLYPROPYLENE + 0.5% benzophenone (Tinuvin 531) | 4.5 | 5.2 | 5.6 | 8 | 6 | 50 |
| POLYPROPYLENE + 0.9% benz-triazole derivative (Tinuvin P) | 4.3 | — | 14 | 47 | | |

We claim:
1. A compound of the formula:

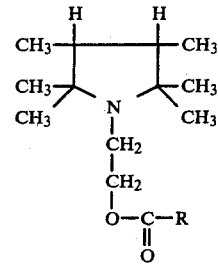

wherein R is the radical $C_nH_{2n+1}$, n having a value from 4 to 17.

2. The compound of claim 1 wherein n is 11.
3. The compound of claim 1 wherein n is 15.
4. A polyolefin composition stabilized against the effects of UV-radiations comprising a polyolefin and a stabilizing amount of one or more of the compounds of claim 1.
5. A method of stabilizing a polyolefin composition against the effects of UV-radiations which comprises adding to said composition a stabilizing amount of one or more of the compounds of claim 1.

* * * * *